US009365609B2

(12) United States Patent
Gutman et al.

(10) Patent No.: US 9,365,609 B2
(45) Date of Patent: *Jun. 14, 2016

(54) PROCESS FOR PREPARING A CRYSTALLINE FORM OF HALOBETASOL PROPIONATE

(71) Applicant: Taro Pharmaceutical North America, Inc., Grand Cayman (KY)

(72) Inventors: Daniella Gutman, Rishon (IL); Shimon Chernyak, Yokneam L-Lit (IL)

(73) Assignee: TARO PHARMACEUTICALS NORTH AMERICA, INC., Grand Cayman (KY)

( * ) Notice: Subject to any disclaimer, the term of this patent is extended or adjusted under 35 U.S.C. 154(b) by 376 days.

This patent is subject to a terminal disclaimer.

(21) Appl. No.: 13/735,428

(22) Filed: Jan. 7, 2013

(65) Prior Publication Data

US 2013/0217903 A1    Aug. 22, 2013

Related U.S. Application Data

(60) Continuation of application No. 12/632,365, filed on Dec. 7, 2009, now Pat. No. 8,361,997, which is a division of application No. 11/399,732, filed on Apr. 6, 2006, now abandoned.

(60) Provisional application No. 60/669,045, filed on Apr. 7, 2005.

(51) Int. Cl.
*A61K 31/56* (2006.01)
*C07J 5/00* (2006.01)
*C07J 7/00* (2006.01)

(52) U.S. Cl.
CPC . *C07J 7/0085* (2013.01); *C07J 7/00* (2013.01)

(58) Field of Classification Search
CPC ...................................................... C07J 7/0085
USPC .................... 514/177, 179; 552/570, 582, 580
See application file for complete search history.

(56) References Cited

U.S. PATENT DOCUMENTS

| 3,557,158 | A | 1/1971 | Lincoln et al. |
| 4,619,921 | A | 10/1986 | Kalvoda et al. |
| 7,208,485 | B2 | 4/2007 | Adin et al. |
| 8,361,997 | B2 * | 1/2013 | Gutman .................... C07J 7/00 514/177 |
| 2003/0162959 | A1 | 8/2003 | Chernyak et al. |
| 2004/0138191 | A1 | 7/2004 | Adin et al. |
| 2004/0138192 | A1 | 7/2004 | Adin et al. |

OTHER PUBLICATIONS

Thompson, M.D. (1999) "Chemical Development of the Drug Substance Solid Form" in Process Chemistry in the Pharmaceutical Industry. Edited by Gadamasetti, K.G., published by Marcel Dekker, Inc., p. 371-374.*
Meyerson, Allan S., "Molecular Modeling Applications in Crystallization," Cambridge University Press, New York, pp. 77-78, 1999.
International Search Report and Written Opinion of the International Searching Authority issued in Application No. PCT/US2006/013044 dated Dec. 12, 2006.
International Preliminary Report on Patentability of the International Searching Authority issued in Application No. PCT/US2006/013044 dated Oct. 9, 2007.

* cited by examiner

*Primary Examiner* — Scarlett Goon

(57) ABSTRACT

The present invention provides a process for preparing a crystalline form of halobetasol propionate, comprising the step of crystallizing halobetasol propionate from absolute ethanol or a mixture of ethanol and water, wherein the crystalline form of halobetasol propionate is characterized by an x-ray powder diffraction pattern having peaks at 10.0, 11.6, 12.9, 13.4, 14.5, 16.4, 17.6, and 23.5±0.2 degrees 2θ.

19 Claims, 6 Drawing Sheets

PROCESS FOR PREPARING A CRYSTALLINE FORM OF HALOBETASOL PROPIONATE

CROSS REFERENCE TO RELATED APPLICATION

This application is a continuation of U.S. application Ser. No. 12/632,365, now U.S. Pat. No. 8,361,997, which is a divisional of U.S. application Ser. No. 11/399,732, filed Apr. 6, 2006, which claims the benefit under 35 U.S.C. §119(e) of U.S. Provisional Application No. 60/699,045 filed Apr. 7, 2005, the disclosures of which are incorporated by reference in their entirety.

BACKGROUND OF THE INVENTION

1. Technical Field

This invention relates to a process for preparing a crystalline form of halobetasol propionate. The crystalline form of halobetasol propionate is characterized by an x-ray powder diffraction pattern having peaks at 10.0, 11.6, 12.9, 13.4, 14.5, 16.4, 17.6, and 23.5±0.2 degrees 2θ.

2. Background Art

Halobetasol propionate ((6α,11β,16β)-21-chloro-6,9-difluoro-11-hydroxy-16-methyl-17-(1-oxopropoxy)pregna-1,4-diene-3,20-dione; CAS #66852-54-8) is a high potency corticosteroid indicated for the relief of the inflammatory and pruritic manifestations of corticosteroid-responsive dermatoses. Halobetasol propionate has the following chemical structure:

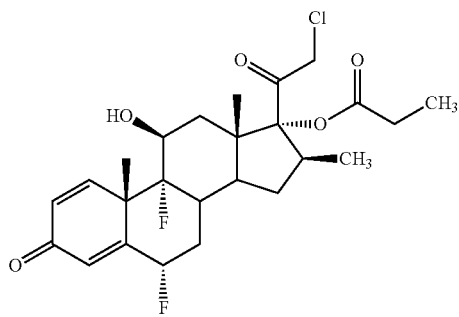

U.S. Pat. No. 4,619,921 (the '921 patent), issued in 1986, discloses the synthesis of halobetasol propionate. The '921 patent further discloses recrystallization of halobetasol propionate using a solvent system containing a mixture of methylene chloride and ether. The '921 patent discloses the melting point of the obtained crystalline form of halobetasol propionate (i.e., 220-221° C.), but does not expressly disclose the x-ray diffraction pattern.

Since 1992, halobetasol propionate has been marketed and on sale under the tradename ULTRAVATE® (Bristol-Myers Squibb Co., Princeton, N.J.) as an ointment and a cream. Both ULTRAVATE® ointment and ULTRAVATE® cream contain 0.05% (w/w) halobetasol propionate as the active ingredient. Halobetasol propionate is soluble in organic solvents, but is insoluble in water. Thus, halobetasol propionate is completely dissolved in organic solvent-based ULTRAVATE® ointment, but remains as a suspended solid in water-based ULTRAVATE® cream. The literature contains no published characterization data regarding the specific crystalline form of halobetasol propionate used or contained in ULTRAVATE® ointment and cream.

U.S. Patent Application Nos. 2004/0138191 (the '191 application) and 2004/0138192 (the '192 application) disclose x-ray powder diffraction, infrared, and differential scanning calorimetry characterization data for a total of six (6) crystalline forms of halobetasol propionate (i.e., Forms I, II, III, IV, V and VI). According to the '191 and '192 applications, crystallization using methylene chloride/ether (the solvent system disclosed in the '921 patent) at a ratio of 5:1 results in crystalline Form I of halobetasol propionate.

The six (6) crystalline forms of halobetasol propionate disclosed in the '191 and '192 applications were prepared using eight (8) different solvent systems. Apparently, there is no predictable correlation between the nature of the solvent system used (e.g., polarity, functional groups, hydrogen bonding ability) and the crystalline form of halobetasol propionate obtained. For example, crystallization from isopropanol, methanol/water, and methanol (all alcoholic solvent systems) yields three (3) different crystalline forms of halobetasol propionate (i.e., Forms III, IV, and VI, respectively). In addition, while crystallization from methylene chloride provides Form III of halobetasol propionate, crystallization from methylene chloride/ether provides Form I of halobetasol propionate.

A disadvantage of the crystallization processes disclosed in the '191 and '192 applications is that five (5) of the eight (8) solvent systems contain methylene chloride, toluene, or methanol. Therefore, these five (5) solvent systems are toxic. In addition, only three (3) of the eight (8) solvent systems disclosed in the '191 and '192 applications provide Form III of halobetasol propionate. Preliminary studies from our laboratory indicate that Form III of halobetasol propionate matches the crystalline form of halobetasol propionate present in ULTRAVATE® cream.

There is a continuing need for a process for preparing a crystalline form of halobetasol propionate, such as the crystalline form present in the commercial ULTRAVATE® cream. There is a need for a process that provides a crystalline form of halobetasol propionate in high yield and substantially free of impurities, employs a non-toxic solvent system, and is suitable for commercial scale use.

SUMMARY OF THE INVENTION

The present invention provides a process for preparing a crystalline form of halobetasol propionate, comprising the step of crystallizing halobetasol propionate from absolute ethanol or a mixture of ethanol and water, wherein the crystalline form of halobetasol propionate is characterized by an x-ray powder diffraction pattern having peaks at 10.0, 11.6, 12.9, 13.4, 14.5, 16.4, 17.6, and 23.5±0.2 degrees 2θ.

The crystalline form of halobetasol propionate is further characterized by an infrared spectrum having absorption peaks at 1741, 1709, 1665, 1627, and 1611±4 cm$^{-1}$. The crystalline form of halobetasol propionate is further characterized by a melting point of about 220° C. to about 221° C.

Preferably, the crystallization step is performed using absolute ethanol.

Preferably, the crystallizing step is performed using a mixture of ethanol and water at a vol/vol ratio between about 50:50 to about 100:0. Preferably, the crystallizing step is performed using a mixture of ethanol and water at a vol/vol ratio between about 50:50 to about 67:33. Preferably, the crystallizing step is performed using a mixture of ethanol and water at a vol/vol ratio of about 50:50.

Preferably, the crystallizing step is performed by a process comprising the steps of:

(a) preparing a solution of halobetasol propionate in absolute ethanol or a mixture of ethanol and water; and (b) inducing precipitation of a crystalline form of halobetasol propionate.

Preferably, step (a) is performed by heating absolute ethanol or a mixture of halobetasol propionate, ethanol, and water to an elevated temperature. More preferably, step (a) is performed by heating a mixture of halobetasol propionate, ethanol, and water to a temperature of about 60° C. to about 80° C.

Preferably, step (b) is performed by cooling the prepared solution. More preferably, step (b) is performed by cooling the prepared solution to a temperature of about 0° C. to about 25° C.

Preferably, step (b) is performed by adding water to the prepared solution. More preferably, step (b) is performed by adding water to the prepared solution over the course of about 30 minutes to about 90 minutes.

Preferably, the process for preparing a crystalline form of halobetasol propionate further comprises the step of isolating the crystallized halobetasol propionate from the mixture of ethanol and water. Preferably, the isolating step is performed by filtration.

Preferably, the crystallizing step is repeated at least once.

Preferably, the crystalline form of halobetasol propionate is prepared as a single batch of at least about 100 grams. More preferably, the crystalline form of halobetasol propionate is prepared as a single batch of at least about 500 grams. More preferably, the crystalline form of halobetasol propionate is prepared as a single batch of at least about one (1) kilogram.

The present invention further provides a process for preparing a crystalline form of halobetasol propionate, comprising the steps of:

(a) crystallizing halobetasol propionate from a first ethanol;

(b) isolating the crystallized halobetasol propionate from the first ethanol;

(c) crystallizing the isolated halobetasol propionate from a second ethanol; and (d) isolating the crystallized halobetasol propionate from the second ethanol, wherein the crystalline form of halobetasol propionate is characterized by an x-ray powder diffraction pattern having peaks at 10.0, 11.6, 12.9, 13.4, 14.5, 16.4, 17.6, and 23.5±0.2 degrees 2θ.

The present invention further provides a process for preparing a crystalline form of halobetasol propionate, comprising the steps of:

(a) crystallizing halobetasol propionate from a first mixture of ethanol and water;

(b) isolating the crystallized halobetasol propionate from the first mixture of ethanol and water;

(c) crystallizing the isolated halobetasol propionate from a second mixture of ethanol and water; and (d) isolating the crystallized halobetasol propionate from the second mixture of ethanol and water, wherein the crystalline form of halobetasol propionate is characterized by an x-ray powder diffraction pattern having peaks at 10.0, 11.6, 12.9, 13.4, 14.5, 16.4, 17.6, and 23.5±0.2 degrees 2θ.

Preferably, the first mixture contains ethanol and water at a vol/vol ratio of about 67:33. Preferably, the second mixture contains ethanol and water at a vol/vol ratio of about 50:50.

Preferably, the crystalline form of halobetasol propionate has a purity of at least about 99.0% (w/w). More preferably, the crystalline form of halobetasol propionate has a purity of at least about 99.8% (w/w).

Preferably, the crystalline form of halobetasol propionate contains about 0.1% (w/w) or less of each individual impurity. Examples of impurities include, but are not limited to, diflorasone, diflorasone 17-propionate, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one].

Preferably, the crystalline form of halobetasol propionate contains about 0.02% (w/w) or less of diflorasone. Preferably, the crystalline form of halobetasol propionate contains about 0.02% (w/w) or less of halobetasol. Preferably, the crystalline form of halobetasol propionate contains about 0.03% (w/w) or less of diflorasone 21-propionate. Preferably, the crystalline form of halobetasol propionate contains about 0.03% (w/w) or less of diflorasone 17-propionate 21-mesylate. Preferably, the crystalline form of halobetasol propionate contains about 0.05% (w/w) or less of 6α,9α-difluoro-11β-hydroxy-16β-methyl-3-oxoandrosta-1,4-diene-17(R)-spiro-2'-[4'-chloro-5'-ethylfuran-3-(2'H)-one].

The present invention further provides a commercial scale composition of a crystalline form of halobetasol propionate prepared by the process of the present invention.

The present invention further provides a commercial scale composition of a crystalline form of halobetasol propionate characterized by an x-ray powder diffraction pattern having peaks at 10.0, 11.6, 12.9, 13.4, 14.5, 16.4, 17.6, and 23.5±0.2 degrees 2θ, wherein the composition contains about 0.1% or less of each of diflorasone, diflorasone 17-propionate, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one].

Preferably, the commercial scale composition contains about 0.1% (w/w) or less of each impurity present in the composition. Preferably, the commercial scale composition contains about 0.05% (w/w) or less of each of diflorasone, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one]. Preferably, the commercial scale composition contains about 0.03% (w/w) or less of each of diflorasone, halobetasol, diflorasone 21-propionate, and diflorasone 17-propionate 21-mesylate. Preferably, the commercial scale composition contains about 0.02% (w/w) or less of each of diflorasone and halobetasol.

Preferably, the commercial scale composition has a purity of at least about 99.5% (w/w). More preferably, the commercial scale composition has a purity of at least about 99.7% (w/w). More preferably, the commercial scale composition has a purity of at least about 99.8% (w/w).

Preferably, the commercial scale composition is produced as a single batch of at least about 500 grams. More preferably, the commercial scale composition is produced as a single batch of at least about one kilogram.

BRIEF DESCRIPTION OF THE DIAGRAMS

DETAILED DESCRIPTION OF THE INVENTION

Definitions

Figure 1:
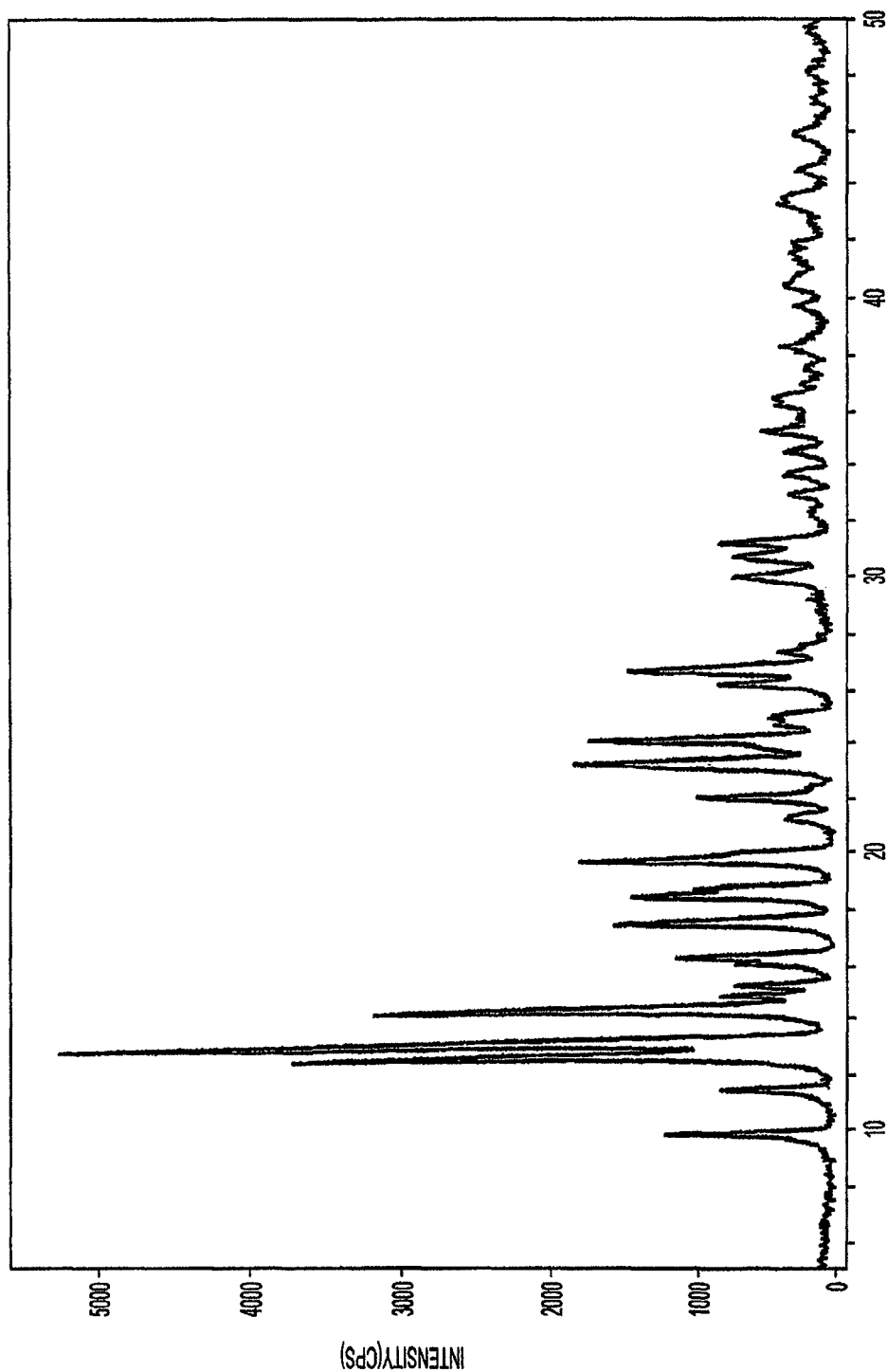
FIG. 1 depicts an x-ray powder diffraction (XRPD) pattern of the present crystalline form of halobetasol propionate.

"Crystalline form" refers to a solid chemical compound that provides a pattern of peaks when analyzed by x-ray powder diffraction; this includes polymorphs, solvates, hydrates, and desolvated solvates; "crystallization" refers to a process wherein a chemical compound that is dissolved or suspended in a solvent system becomes a crystalline form; "solvent system" refers to a solvent or mixture of solvents; for purposes of the present invention "crystallization" and "recrystallization" are used interchangeably; "isolating" refers to separating a chemical compound (e.g., a crystalline form) from a reaction mixture (e.g., a solvent system); according to the present invention, an isolated compound typically has a purity of at least about 90% (w/w); "batch size" refers to the amount of a product compound (e.g., a crystalline form) produced during a chemical manufacturing step (e.g., a crystallization step); "rolling crystallization" refers to a solvent-mediated transformation of a solid compound into a crystalline form (See generally, *Molecular Modeling Applications in Crystallization*, Allan Myerson ed., Cambridge Univ. Press, 1999, 77-78); "ethanol" refers to a compound having the formula $C_2H_5OH$; "reflux temperature" refers to the temperature at which a liquid boils; "purity" refers to the percentage by weight (% w/w) of one component of a mixture; "purifying" refers to increasing the purity of a compound; "pharmaceutical grade" refers to a purity of at least about 99.0% (w/w); "precipitation" refers to a process wherein a solid forms in a solution; "slurrying" refers to agitating a suspension, e.g., by stirring; "suspension" refers to a fluid that contains solid (i.e., undissolved) particles of a compound; "HPLC" refers to high performance liquid chromatography; "composition" refers to a solid chemical compound that has been synthesized by a chemical reaction, isolated from the reaction mixture, and optionally purified by (re)crystallization, together with any impurities that are present with the compound; "commercial scale composition" refers to a composition that is produced as a single batch of at least about 100 grams of the composition, and "laboratory scale" refers to one that has less than about 100 grams of the composition.

Unless otherwise indicated, as expressed in the present specification as well as in the set of claims as % weight refers to % wt/wt. % weight refers to percentage of the weight of the referenced compound as compared to the total weight of the composition. For purposes of the present invention, the term "about" refers to +/−10% of a specified value, as recognized by one skilled in the art.

The present invention provides a process for preparing a crystalline form of halobetasol propionate, comprising the step of crystallizing halobetasol propionate from absolute ethanol (100%). The crystalline form of halobetasol propionate prepared by the process of the present invention is characterized by an x-ray powder diffraction pattern having peaks at 10.0, 11.6, 12.9, 13.4, 14.5, 16.4, 17.6, and 23.5±0.2 degrees 2θ.

The present invention provides a process for preparing a crystalline form of halobetasol propionate, comprising the step of crystallizing halobetasol propionate from a mixture of ethanol and water. The crystalline form of halobetasol propionate prepared by the process of the present invention is characterized by an x-ray powder diffraction pattern having peaks at 10.0, 11.6, 12.9, 13.4, 14.5, 16.4, 17.6, and 23.5±0.2 degrees 2 θ.

Suitable processes for preparing halobetasol propionate are known in the art. For example, halobetasol propionate may be prepared by the following three steps: (a) reacting diflorasone with an alkyl orthopropionate reagent; (b) reacting the resulting diflorasone 17-propionate with methanesulfonyl chloride; and (c) reacting the resulting diflorasone 17-propionate-21-mesylate with lithium chloride to form halobetasol propionate. This three-step process is described in detail in our copending application, U.S. Patent Application No. 2003/0162959 A1 (the '959 application). An alternative method for preparing halobetasol propionate is disclosed in U.S. Pat. No. 4,619,921 (the '921 patent). The '959 application and '921 patent are incorporated herein by reference in their entireties.

The diflorasone used in step (a) of the above-mentioned halobetasol propionate synthesis process may be prepared by known methods (See, e.g., U.S. Pat. No. 3,557,158 (Example 24A), incorporated herein by reference in its entirety). For example, diflorasone may be prepared by hydrolysis of diflorasone diacetate using a process analogous to the process disclosed in Example IV of the '959 application. Diflorasone diacetate is commercially available (Sigma-Aldrich, St. Louis, Mo.), or may be prepared by known methods.

The crystallizing step may be performed using any suitable method. Suitable methods for performing the crystallizing step include, but are not limited to, solution crystallization and rolling crystallization. Preferably, the crystallizing step is performed by solution crystallization. Preferably, solution crystallization comprises the steps of:

(a) preparing a solution of halobetasol propionate in absolute ethanol; and (b) inducing precipitation of a crystalline form of halobetasol propionate.

Preferably, solution crystallization comprises the steps of:

(a) preparing a solution of halobetasol propionate in a mixture of ethanol and water; and (b) inducing precipitation of a crystalline form of halobetasol propionate.

Preferably, rolling crystallization comprises the steps of:

(a) preparing a suspension of halobetasol propionate in a mixture of ethanol and water, and (b) slurrying the suspension to form a crystalline form of halobetasol propionate.

The step (a) solution or step (a) suspension is prepared from halobetasol propionate. The halobetasol propionate may be crystalline, amorphous, semisolid, syrup, a mixture thereof, or the like. Crystalline halobetasol propionate may include polymorphs, solvates, clathrates, and the like, and mixtures thereof. Exemplary crystalline forms of halobetasol propionate include, but are not limited to, halobetasol propionate Forms I, II, III, IV, V, and VI (See the '191 and '192 applications).

Preferably, the step (a) solution or step (a) suspension is prepared from crude halobetasol propionate. "Crude halobetasol propionate" refers to halobetasol propionate that is synthesized by a chemical reaction and isolated from the reaction mixture, but not further purified. Processes for preparing crude halobetasol propionate include, but are not limited to, the processes set forth in U.S. Pat. No. 4,619,921 (Example 5) and U.S. Patent Application No. 2003/0162959 A1 (Example VIII).

With respect to the solution crystallization process, the step (a) solution may be prepared using any suitable method. Suitable methods for preparing the step (a) solution include, but are not limited to, adding halobetasol propionate to ethanol, and adding halobetasol propionate to a mixture of ethanol and water.

Preferably, the step (a) solution is prepared by heating a mixture of halobetasol propionate, ethanol, and water to an elevated temperature. More preferably, the step (a) solution is prepared by heating a mixture of halobetasol propionate, ethanol, and water to a temperature of about 60° C. to about 80° C. More preferably, the step (a) solution is prepared by heating a mixture of halobetasol propionate, ethanol, and water to about the reflux temperature of the solution.

Optionally, the step (a) solution may be filtered prior to step (b). Preferably, the step (a) solution is hot filtered at an elevated temperature prior to step (b). More preferably, the step (a) solution is hot filtered at a temperature of about 60° C. to about 80° C. prior to step (b). More preferably, the step (a) solution is hot filtered at a temperature of about 70° C. prior to step (b).

With respect to the optional filtering step, the step (a) solution may be further purified by treatment with activated charcoal prior to filtering. Activated charcoal is commercially available from NORIT Nederland B.V. (the Netherlands).

The optional filtering step may be performed using a filter aid. Suitable filter aids include, but are not limited to, diatomaceous earth (e.g., the active ingredient in CELITE®, manufactured and sold by World Minerals, Inc. (Santa Barbara, Calif.)).

With respect to step (b) of the solution crystallization process, the step (b) precipitation may be induced using any suitable method. Suitable methods for inducing precipitation include, but are not limited to, adding water to the step (a) solution, and cooling the step (a) solution.

Preferably, the step (b) precipitation is induced by slowly adding water to the step (a) solution. More preferably, the step (b) precipitation is induced by adding water to the step (a) solution over the course of about 30 minutes to about 90 minutes. More preferably, the step (b) precipitation is induced by adding water to the step (a) solution over the course of about one (1) hour.

Preferably, the step (b) precipitation is induced by adding water to the step (a) solution at an elevated temperature. More preferably, the step (b) precipitation is induced by adding water to the step (a) solution at a temperature of about 60° C. to about 80° C. More preferably, the step (b) precipitation is induced by adding water to the step (a) solution at a temperature of about 70° C.

Preferably, the step (b) precipitation is induced by cooling the step (a) solution. Preferably, the step (b) precipitation is induced by cooling the step (a) solution to a temperature of about 0° C. to about 25° C. More preferably, the step (b) precipitation is induced by cooling the step (a) solution to a temperature of about 18° C. to about 25° C.

Any suitable cooling rate may be used in the step (b) precipitation. For example, the step (b) precipitation may be induced by cooling the step (a) solution over the course of about five (5) minutes to about one (1) hour.

With respect to the rolling crystallization process, the step (a) suspension of halobetasol propionate may be prepared using any suitable method. Suitable methods for preparing the step (a) suspension include, but are not limited to, adding halobetasol propionate to a mixture of ethanol and water, optionally with cooling.

With respect to step (b) of the rolling crystallization process, the slurrying step (b) may be performed using any suitable method. Suitable methods for performing the slurrying step (b) include, but are not limited to, stirring the step (a) suspension.

The slurrying step (b) may be performed at any suitable temperature. Preferably, the slurrying step (b) is performed at about ambient temperature or below. Preferably, the slurrying step (b) is performed at a temperature of about 0° C. to about 25° C. More preferably, the slurrying step (b) is performed at a temperature of about 18° C. to about 25° C.

With respect to the crystallizing step of the present invention (e.g., performed using solution crystallization or rolling crystallization), the crystallizing step may be performed using halobetasol propionate, ethanol, and water in any suitable proportions. Preferably, the crystallizing step is performed at an ethanol to halobetasol propionate ratio of about 3:1 to about 50:1 (w/w). More preferably, the crystallizing step is performed at an ethanol to halobetasol propionate ratio of about 5:1 to about 25:1 (w/w). More preferably, the crystallizing step is performed at an ethanol to halobetasol propionate ratio of about 10:1 (w/w).

Preferably, the crystallizing step is performed at an ethanol to water ratio of about 50:50 (v/v) to about 100:0 (v/v). More preferably, the crystallizing step is performed at an ethanol to water ratio of about 50:50 (v/v) to about 67:33 (v/v). More preferably, the crystallizing step is performed at an ethanol to water ratio of about 50:50 (v/v).

Preferably, the process of the present invention further comprises the step of isolating the crystalline form of halobetasol propionate from the mixture of ethanol and water after the crystallizing step. Suitable isolation methods include, but are not limited to, filtration, centrifugation, and decantation. Preferably, the isolating step is performed by filtration.

Preferably, the isolated crystalline form of halobetasol propionate is dried. Preferably, the isolated crystalline form of halobetasol propionate is dried at an elevated temperature. More preferably, the isolated crystalline form of halobetasol propionate is dried at a temperature of about 60° C. to about 80° C. More preferably, the isolated crystalline form of halobetasol propionate is dried at a temperature of about 65° C. to about 75° C.

Preferably, the isolated crystalline form of halobetasol propionate is dried at a reduced pressure. More preferably, the isolated crystalline form of halobetasol propionate is dried at a pressure of about 200 mbar or less. More preferably, the isolated crystalline form of halobetasol propionate is dried at a pressure of about 100 mbar or less.

Repeated crystallization may increase the purity of the present crystalline form of halobetasol propionate. Preferably, the crystallizing step is repeated at least once. In a preferred embodiment, the process for preparing the present crystalline form of halobetasol propionate comprises the steps of:

(a) crystallizing halobetasol propionate from a first ethanol;

(b) isolating the crystallized halobetasol propionate from the first ethanol;

(c) crystallizing the isolated halobetasol propionate from a second ethanol; and (d) isolating the crystallized halobetasol propionate from the second ethanol.

In another preferred embodiment, the process for preparing the present crystalline form of halobetasol propionate comprises the steps of:

(a) crystallizing halobetasol propionate from a first mixture of ethanol and water;

(b) isolating the crystallized halobetasol propionate from the first mixture of ethanol and water;

(c) crystallizing the isolated halobetasol propionate from a second mixture of ethanol and water; and (d) isolating the crystallized halobetasol propionate from the second mixture of ethanol and water.

Preferably, the ratio of ethanol to water in the first mixture is about 50:50 (v/v). Preferably, the ratio of ethanol to water in the second mixture is about 67:33 (v/v).

The present crystalline form of halobetasol propionate is characterized by an x-ray powder diffraction pattern having peaks at 10.0, 11.6, 12.9, 13.4, 14.5, 16.4, 17.6, and 23.5±0.2 degrees 2θ. The present crystalline form of halobetasol propionate is further characterized by an infrared spectrum having absorption peaks at 1741, 1709, 1665, 1627, and 1611±4 $cm^{-1}$. The present crystalline form of halobetasol propionate is further characterized by a melting point of about 220° C. to about 221° C.

Preliminary studies from our laboratory indicate that the present crystalline form of halobetasol propionate matches the crystalline form of halobetasol propionate present in ULTRAVATE® cream. An advantage of the present crystallization process is that it provides the commercial crystalline form of halobetasol propionate.

A further advantage of the present invention is that the crystallizing step is performed using ethanol or a mixture of ethanol and water, which are non-toxic.

In a preferred embodiment, the process of the present invention is performed at a commercial scale. Preferably, the present crystalline form of halobetasol propionate is produced as a single batch of at least about 100 grams. More preferably, the present crystalline form of halobetasol propionate is produced as a single batch of at least about 500 grams. More preferably, the present crystalline form of halobetasol propionate is produced as a single batch of at least about one (1) kilogram.

A further advantage of the present invention is that the present crystalline form of halobetasol propionate is produced in high yield. Preferably, the present crystalline form of halobetasol propionate is produced in a yield of at least about 80% (w/w). More preferably, the present crystalline form of halobetasol propionate is produced in a yield of at least about 90% (w/w). More preferably, the present crystalline form of halobetasol propionate is produced in a yield of at least about 95% (w/w).

In a preferred embodiment, the present crystallization process is suitable for the production of pharmaceutical grade halobetasol propionate from crude halobetasol propionate. Preferably, the present crystalline form of halobetasol propionate has a purity of at least about 99.0% (w/w). More preferably, the present crystalline form of halobetasol propionate has a purity of at least about 99.5% (w/w). More preferably, the present crystalline form of halobetasol propionate has a purity of at least about 99.6% (w/w). More preferably, the present crystalline form of halobetasol propionate has a purity of at least about 99.7% (w/w). More preferably, the present crystalline form of halobetasol propionate has a purity of at least about 99.8% (w/w). The purity of the present crystalline form of halobetasol propionate may be determined as set forth below (See Methodology and Protocols).

Preferably, the present crystalline form of halobetasol propionate contains about 0.1% (w/w) or less of each individual impurity. Examples of possible impurities include, but are not limited to, diflorasone, diflorasone 17-propionate, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethyl-furan-3-(2'H)-one].

Preferably, the present crystalline form of halobetasol propionate contains about 0.1% (w/w) or less of diflorasone. More preferably, the present crystalline form of halobetasol propionate contains about 0.05% (w/w) or less of diflorasone. More preferably, the present crystalline form of halobetasol propionate contains about 0.02% (w/w) or less of diflorasone.

Preferably, the present crystalline form of halobetasol propionate contains about 0.1% (w/w) or less of diflorasone 17-propionate.

Preferably, the present crystalline form of halobetasol propionate contains about 0.1% (w/w) or less of halobetasol. More preferably, the present crystalline form of halobetasol propionate contains about 0.05% (w/w) or less of halobetasol. More preferably, the present crystalline form of halobetasol propionate contains about 0.02% (w/w) or less of halobetasol.

Preferably, the present crystalline form of halobetasol propionate contains about 0.1% (w/w) or less of diflorasone 21-propionate. More preferably, the present crystalline form of halobetasol propionate contains about 0.05% (w/w) or less of diflorasone 21-propionate. More preferably, the present crystalline form of halobetasol propionate contains about 0.03% (w/w) or less of diflorasone 21-propionate.

Preferably, the present crystalline form of halobetasol propionate contains about 0.1% (w/w) or less of diflorasone 17-propionate 21-mesylate. More preferably, the present crystalline form of halobetasol propionate contains about 0.05% (w/w) or less of diflorasone 17-propionate 21-mesylate. More preferably, the present crystalline form of halobetasol propionate contains about 0.03% (w/w) or less of diflorasone 17-propionate 21-mesylate.

Preferably, the present crystalline form of halobetasol propionate contains about 0.1% (w/w) or less of 6α,9α-difluoro-11β-hydroxy-16β-methyl-3-oxoandrosta-1,4-diene-17(R)-spiro-2'-[4'-chloro-5'-ethylfuran-3-(2'H)-one]. More preferably, the present crystalline form of halobetasol propionate contains about 0.05% (w/w) or less of 6α,9α-difluoro-11β-hydroxy-16β-methyl-3-oxoandrosta-1,4-diene-17(R)-spiro-2'-[4'-chloro-5'-ethylfuran-3-(2'H)-one].

In a preferred embodiment, the present invention provides a commercial scale composition of a crystalline form of halobetasol propionate prepared by the process of the present invention.

In a preferred embodiment, the present invention provides a commercial scale composition of a crystalline form of halobetasol propionate characterized by an x-ray powder diffraction pattern having peaks at 10.0, 11.6, 12.9, 13.4, 14.5, 16.4, 17.6, and 23.5±0.2 degrees 2θ, wherein the composition contains about 0.1% or less of each of diflorasone, diflorasone 17-propionate, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one]. Preferably, the commercial scale composition contains about 0.1% (w/w) or less of each impurity present in the composition.

Preferably, the commercial scale composition contains about 0.05% (w/w) or less of at least one of diflorasone, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one]. More preferably, the commercial scale composition contains about 0.05% (w/w) or less of each of diflorasone, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one].

Preferably, the commercial scale composition contains about 0.03% (w/w) or less of at least one of diflorasone, halobetasol, diflorasone 21-propionate, or diflorasone 17-propionate 21-mesylate. More preferably, the commercial scale composition contains about 0.03% (w/w) or less of each of diflorasone, halobetasol, diflorasone 21-propionate, and diflorasone 17-propionate 21-mesylate.

Preferably, the commercial scale composition contains about 0.02% (w/w) or less of at least one of diflorasone or halobetasol. More preferably, the commercial scale composition contains about 0.02% (w/w) or less of each of diflorasone and halobetasol.

Preferably, the commercial scale composition has a purity of at least about 99.5% (w/w). More preferably, the commercial scale composition has a purity of at least about 99.6% (w/w). More preferably, the commercial scale composition has a purity of at least about 99.7% (w/w). More preferably, the commercial scale composition has a purity of at least about 99.8% (w/w).

As stated above, "composition" refers to a solid chemical compound that has been synthesized by a chemical reaction, isolated from the reaction mixture, and optionally purified by (re)crystallization, together with any impurities that are present with the compound. Impurities are intended to include, but are not limited to, undesired side-products formed during chemical synthesis. Examples of impurities that may be present in the composition include, but are not limited to, diflorasone, diflorasone 17-propionate, halobetasol, diflorasone 21-propionate, diflorasone 17-propionate 21-mesylate, and 6α,9α-difluoro-11β-hydroxy-16β-methyl-3-oxoandrosta-1,4-diene-17(R)-spiro-2'-[4'-chloro-5'-ethylfuran-3-(2'H)-one].

As stated above, "commercial scale composition" refers to a composition that is produced as a single batch of at least about 100 grams of the composition. Preferably, the composition is produced as a single batch of at least about 500 grams. More preferably, the composition is produced as a single batch of at least about one (1) kilogram.

According to the invention, commercial scale compositions include, but are not limited to, commercial scale compositions that have not been subjected to HPLC (high pressure liquid chromatography) purification, commercial scale compositions that have not been subjected to recrystallization, and commercial scale compositions that have not been subjected to any purification procedure.

In a preferred embodiment, the present invention provides a pharmaceutical formulation comprising the present crystalline form of halobetasol propionate. Further, there is provided a process for preparing such a pharmaceutical formulation, comprising the step of mixing the present crystalline form of halobetasol propionate with at least one pharmaceutically acceptable excipient.

The present crystalline form of halobetasol propionate may, for example, conveniently be formulated for topical, oral, buccal, sublingual, parenteral, local or rectal administration. Topical pharmaceutical formulations are preferred, such as creams, ointments, gels, pastes, foams, tinctures, solutions, and the like, which contain from about 0.005% (w/w) to about 0.1% (w/w) of the present crystalline form of halobetasol propionate.

Ointments, creams and gels, may, for example, be formulated with an aqueous or oily base with the addition of a suitable thickening agent, gelling agent, and/or solvent. Such bases may thus, for example, include water and/or an oil such as liquid paraffin or a vegetable oil such as arachis oil or castor oil, or a solvent such as polyethylene glycol. Thickening agents and gelling agents that may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilizing agents, dispersing agents, suspending agents or thickening agents. Powders for external application may be formed with the aid of any suitable powder base, for example, talc, lactose or starch. Drops may be formulated with an aqueous or non-aqueous base also comprising one or more dispersing agents, solubilizing agents, suspending agents or preservatives.

If appropriate, the formulations of the invention may be buffered by the addition of suitable buffering agents.

Topical preparations may be administered by one or more applications per day to the affected area; over skin areas occlusive dressings may advantageously be used. Continuous or prolonged delivery may be achieved by an adhesive reservoir system.

For internal administration the compounds according to the invention may, for example, be formulated in conventional manner for oral, parenteral or rectal administration. Formulations for oral administration include syrups, elixirs, powders, granules, tablets and capsules which typically contain conventional excipients such as binding agents, fillers, lubricants, disintegrants, wetting agents, suspending agents, emulsifying agents, preservatives, buffer salts, flavoring, coloring and/or sweetening agents as appropriate.

Preferred forms of preparation for internal administration are dosage unit forms i.e. tablets and capsules. In general terms, preparations for internal administration may contain from 0.01 to 10% (w/w) of the present crystalline form of halobetasol propionate dependent upon the type of preparation involved. The daily dose may vary from 0.1 mg to 60 mg, e.g. 5-30 mg, dependent on the condition being treated, and the duration of treatment desired.

Slow release or enteric coated formulations may be advantageous, particularly for the treatment of inflammatory bowel disorders.

Methodology and Protocols

X-Ray Powder Diffraction

X-ray powder diffraction (XRPD) patterns were obtained using a Rigaku X-ray diffractometer Ultima 2200 with a Cu $K_\alpha$ (Ni) radiation source. The samples were run over the range from 5° to 40° with a step size of 0.02° at a rate of 2 steps/second. The present crystalline form of halobetasol propionate is characterized by XRPD peaks at 10.0, 11.6, 12.9, 13.4, 14.5, 16.4, 17.6, and 23.5±0.2 degrees 2θ. FIG. 1 depicts a typical x-ray powder diffraction pattern of the present crystalline form of halobetasol propionate.

Infrared Spectroscopy

Infrared (IR) spectra were obtained using a Nicolet Impact 410 FT-IR instrument using potassium bromide pellets. The present crystalline form of halobetasol propionate is characterized by IR absorption peaks at 1741, 1709, 1665, 1627, and 1611±4 cm$^{-1}$. Proposed peak assignments are provided in the following table:

| Wavenumber, cm$^{-1}$ | Assignment |
|---|---|
| 1741 | C=O |
| 1709 | C=O |
| 1665 | C=O |
| 1627 | C=O |
| 1611 | C=C |

Figure 2:
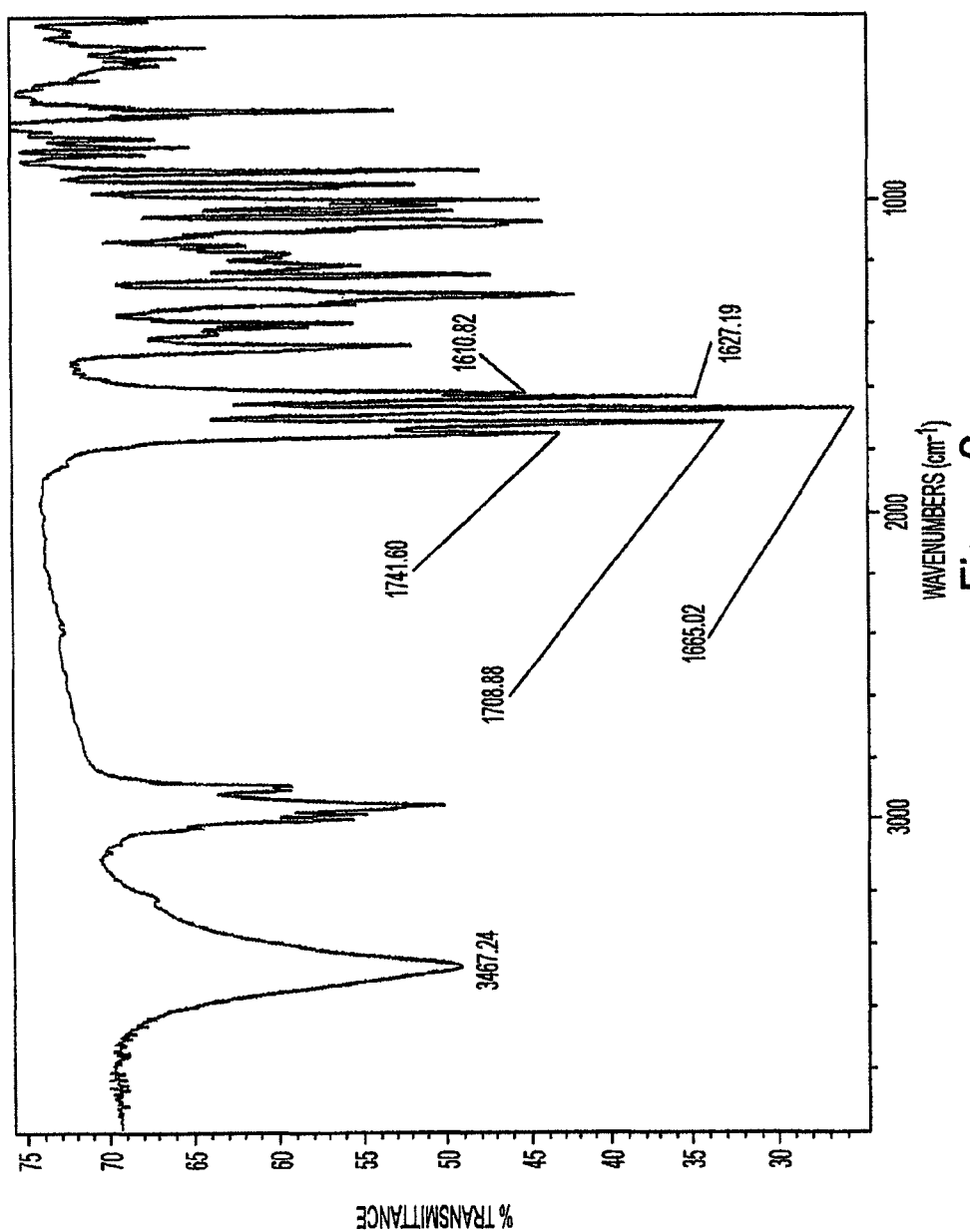
FIG. 2 depicts an infrared (IR) spectrum of the crystalline form of halobetasol propionate at commercial scale, obtained after recrystallizing from a mixture of ethanol and water (v/v ration of about 67:33) and drying in vacuum oven.

FIG. 2 depicts a typical IR spectrum of the present crystalline form of halobetasol propionate.

Melting Point

Melting points were determined by a procedure analogous to the Procedure for Class I, Apparatus I described in section <741> of the United States Pharmacopeia. The melting point of the present crystalline form of halobetasol propionate is about 220° C. to about 221° C.

Purity

Purity was determined using a high performance liquid chromatography (HPLC) instrument with a variable wavelength detector.

(a) Chromatographic Conditions

| | |
|---|---|
| Column | Nova-Pak C18, 4 µm, 3.9*300 mm or equivalent |
| Flow Rate | 1.0 mL/min |
| Column temperature | ambient |
| Detection | UV at 239 nm |
| Injection volume | 20 µL |
| Run time | 15 min for Standard solutions and Known Impurities solution 30 min for Sample solution and Diluent |
| Mobile phase | 45:55 v/v Mixture of Water and Acetonitrile |
| Diluent | Mobile phase |

(b) Known Impurities Solution

The following known impurities were used: diflorasone (6α,9α-difluoro-11β,17,21-trihydroxy-16β-methylpregna-1,4-diene-3,20-dione), diflorasone 17-propionate (6α,9α-difluoro-11β,17,21-trihydroxy-16β-methylpregna-1,4-diene-3,20-dione, 17-propionate), diflorasone 21-propionate (6α,9α-difluoro-11β,17,21-trihydroxy-16β-methylpregna-1,4-diene-3,20-dione, 21-propionate), diflorasone 17-propionate 21-mesylate (6α,9α-difluoro-11β,17,21-trihydroxy-16β-methylpregna-1,4-diene-3,20-dione, 17-propionate 21-mesylate), halobetsol ((6α,11β,16β)-21-chloro-6,9-difluoro-11,17-dihydroxy-16-methylpregna-1,4-diene-3,20-dione), and "Impurity A" (6α,9α-difluoro-11β-hydroxy-16β-methyl-3-oxoandrosta-1,4-diene-17(R)-spiro-2'-[4'-chloro-5'-ethylfuran-3-(2'H)-one]).

Each known impurity was added to a separate 10-mL volumetric flask, and each flask was filled to volume with diluent. The solutions were sonicated to ensure complete dissolution. 5-mL aliquots of each solution were combined in a single 50-mL volumetric flask, and the flask was filled to volume with diluent. A 2-mL aliquot of the resulting solution was added to a 100-mL volumetric flask, together with 20 mg of halobetasol 17-propionate, and the flask was filled to volume with diluent. The solution was sonicated to ensure complete dissolution.

(c) Crystalline Halobetasol Propionate Sample Solution

Approximately 20 mg of the crystalline halobetasol propionate sample to be assayed, accurately weighed, was transferred into a 100-mL volumetric flask, and the flask was filled to volume with diluent. The solution was sonicated to ensure complete dissolution. The sample solution was stable at room temperature for 2 days protected from sunlight.

(d) Crystalline Halobetasol Propionate Standard Solution

Approximately 20 mg of a crystalline halobetasol propionate standard, accurately weighed, was transferred into a 100-mL volumetric flask, and the flask was filled to volume with diluent. The solution was sonicated to ensure complete dissolution. The standard solution was stable at room temperature for 2 days protected from sunlight.

(e) Standard Solution for Determination of Known Impurities

A 5-mL aliquot of the crystalline halobetasol propionate standard solution was added to 100-mL volumetric flask, and the flask was filled to volume with diluent. A 2-mL aliquot of the resulting solution was then added to a 20-mL volumetric flask, and the flask was filled to volume with diluent.

(f) HPLC Protocol

The known impurities solution, six replicate injections of the standard solution for determination of known impurities, and five replicate injections of the crystalline halobetasol propionate standard solution were made.

Resolution factors were calculated according to the United States Pharmacopeia (USP) <621>. The resolution factor between diflorasone and diflorasone 17-propionate, between diflorasone 17-propionate and halobetasol, between diflorasone 21-propionate and diflorasone 17-propionate 21-mesylate, between diflorasone 17-propionate 21-mesylate and halobetasol 17-propionate, and between halobetasol 17-propionate and impurity A was not less than 2.0. The resolution factor between halobetasol and diflorasone 21-propionate was not less than 1.3.

The relative standard deviation of five replicate injections of the crystalline halobetasol propionate standard solution was not more than 2.0%. The relative standard deviation of six replicate injections of the standard solution for determination of known impurities was not more than 10.0%. If necessary, the mobile phase composition and/or flow rate were adjusted to meet the chromatographic parameters.

Typical chromatographic parameters are listed in the following table:

| Compound | Retention Time | Relative Retention Time | Limit of Detection (LOD) | Limit of Quantitation (LOQ) | Relative Response Factor | Resolution |
|---|---|---|---|---|---|---|
| Diflorasone | 2.8 | 0.29 | 0.02% | 0.03% | 1.1 | — |
| Diflorasone 17-propionate | 4.3 | 0.45 | 0.02% | 0.03% | 1.0 | 9.5 |
| Halobetasol | 4.8 | 0.51 | 0.02% | 0.03% | 1.0 | 2.7 |
| Diflorasone 21-propionate | 5.1 | 0.54 | 0.02% | 0.03% | 1.0 | 1.5 |
| Diflorasone 17-propionate 21-mesylate | 7.4 | 0.78 | 0.02% | 0.03% | 0.8 | 10.3 |

-continued

| Compound | Retention Time | Relative Retention Time | Limit of Detection (LOD) | Limit of Quantitation (LOQ) | Relative Response Factor | Resolution |
|---|---|---|---|---|---|---|
| Halobetasol 17-propionate | 9.5 | 1.00 | 0.02% | 0.03% | 1.0 | 7.1 |
| Impurity A | 10.5 | 1.11 | 0.02% | 0.03% | 1.0 | 3.2 |

The limit of detection is the minimum concentration at which the analyte can reliably be detected. The limit of quantitation is the minimum concentration at which the analyte can reliably be quantified. Limits of detection and quantitation were determined by comparing measured signals from samples with known low concentrations of analyte to measured signals from blank samples. The relative response factor is the ratio of slopes provided by calibration curves for analyte and corresponding internal standard (or surrogate and corresponding internal standard). The resolution is the separation of two peaks in terms of their average peak width at base ($t_{R2} > t_{R1}$):

$$\text{Resolution} = \frac{(t_{R2} - t_{R1})}{(w_{b1} + w_{b2})/2} = \frac{2(t_{R2} - t_{R1})}{(w_{b1} + w_{b2})}$$

In the case of two adjacent peaks it may be assumed that $w_{b1} = w_{b2}$, and thus, the width of the second peak may be substituted for the average value: $\text{Resolution} = (t_{R2} - t_{R1})/w_{b2}$.

(g) Calculation of Purity $$\% \text{ Purity} = 100 - (\% \text{ known impurities} + \% \text{ unknown impurities})$$

$$\% \text{ known or unknown impurity} = \frac{S_{imp} \times 100}{S_{sum} \times RRF}$$

$S_{imp}$ = Peak area of impurity obtained from crystalline halobetasol propionate sample solution chromatogram $S_{sum}$ = Sum of the areas of all peaks obtained from crystalline halobetasol propionate sample solution chromatogram $RRF$ = Relative Response Factor (1.0 for unknown impurities)

EXAMPLES

The following Examples 1-4 were performed at a commercial scale. Analogous experiments (Examples 5-8) were performed at a laboratory scale (i.e., batch sizes of less than 100 grams).

Example 1

Synthesis of Crude Halobetasol Propionate

Diflorasone 17-propionate 21-mesylate (1.65 kg) and lithium chloride (1.67 kg) were added to N,N-dimethylacetamide (16 L) in a 100-L reaction vessel. The resulting mixture was stirred under nitrogen at about 80° C. for 3 hours.

The mixture was then cooled to about 20° C. Water (45 L) was added over the course of 50 minutes to the cooled mixture. The resulting mixture was then stirred for about 1 hour at about 20° C. The resulting precipitate was filtered and washed with water (20 L) to provide a wet crude halobetasol propionate (2.84 kg; approximately 1.25 kg on a dry basis).

Example 2

Crystallization of Crude Halobetasol Propionate to Provide a Commercial Scale Composition of a Crystalline Form of Halobetasol Propionate The wet crude halobetasol propionate prepared in Example 1 (2.84 kg) was added to ethanol (14 L) in a 100-L reaction vessel. The resulting mixture was heated at reflux (about 78° C.) for 30 minutes.

The mixture was then cooled to about 70° C. A suspension of activated carbon (0.14-kg) in ethanol (1 L) and a suspension of CELITE 545® (manufactured by Eagle-Picher Minerals Europe (Germany), active ingredient=siliceous earth) (0.14 kg) in ethanol (1 L) were added to the cooled mixture. The resulting mixture was heated at reflux (about 78° C.) for 30 minutes, and then hot filtered.

Water (16 L) was added to the resulting filtrate over the course of 55 minutes at about 70° C. The resulting mixture was stirred at this temperature for 30 minutes. The mixture was cooled to about 25° C., and then stirred for 1 hour at 19-25° C. The resulting precipitate was filtered and washed with a mixture (4 L) of ethanol and water (v/v=50:50), to provide a crystalline form of halobetasol propionate (1.49 kg).

Example 3

Recrystallization of Halobetasol Propionate to Provide a Commercial Scale Composition of a Crystalline Form of Halobetasol Propionate The crystalline form of halobetasol propionate prepared in Example 2 (1.49 kg) was added to ethanol (15 L) in a 150-L reaction vessel. The resulting mixture was heated at reflux (about 78° C.) for 30 minutes, and then transferred to a 100-L reactor.

Water (7.5 L) was added to the mixture over the course of 30 minutes at a temperature of about 71-73° C. The resulting mixture was stirred at 70-71° C. for 30 minutes. The mixture was cooled to 25° C., and then stirred for 1 hour at 20-25° C. The resulting precipitate was filtered and washed with a mixture (3 L) of ethanol and water (v/v=67:33), to provide a crystalline form of halobetasol propionate as wet crystals (1.33 kg).

The wet crystalline form of halobetasol propionate was dried for 12 hours at 70° C. under vacuum (80 mbar) to provide a crystalline form of halobetasol propionate. Yield=1.00 kg.

Example 4

Purity Determination

The purity of the crystalline form of halobetasol propionate prepared in Example 3 was determined using HPLC as set forth above (See Methodology and Protocols). The quantities of known and unknown impurities are listed in the following table:

| Compound | Quantity |
|---|---|
| Diflorasone | <0.02% (LOD) |
| Diflorasone 17-propionate | 0.1% |
| Halobetasol | <0.02% (LOD) |
| Diflorasone 21-propionate | 0.03% |
| Diflorasone 17-propionate 21-mesylate | 0.03% |
| Impurity A | 0.05% |
| Each individual unknown | <0.02% (LOD) |
| Total | 0.2% |

Accordingly, the purity of the crystalline form of halobetasol propionate prepared in Example 3 was 99.8%.

Example 5

Figure 3:
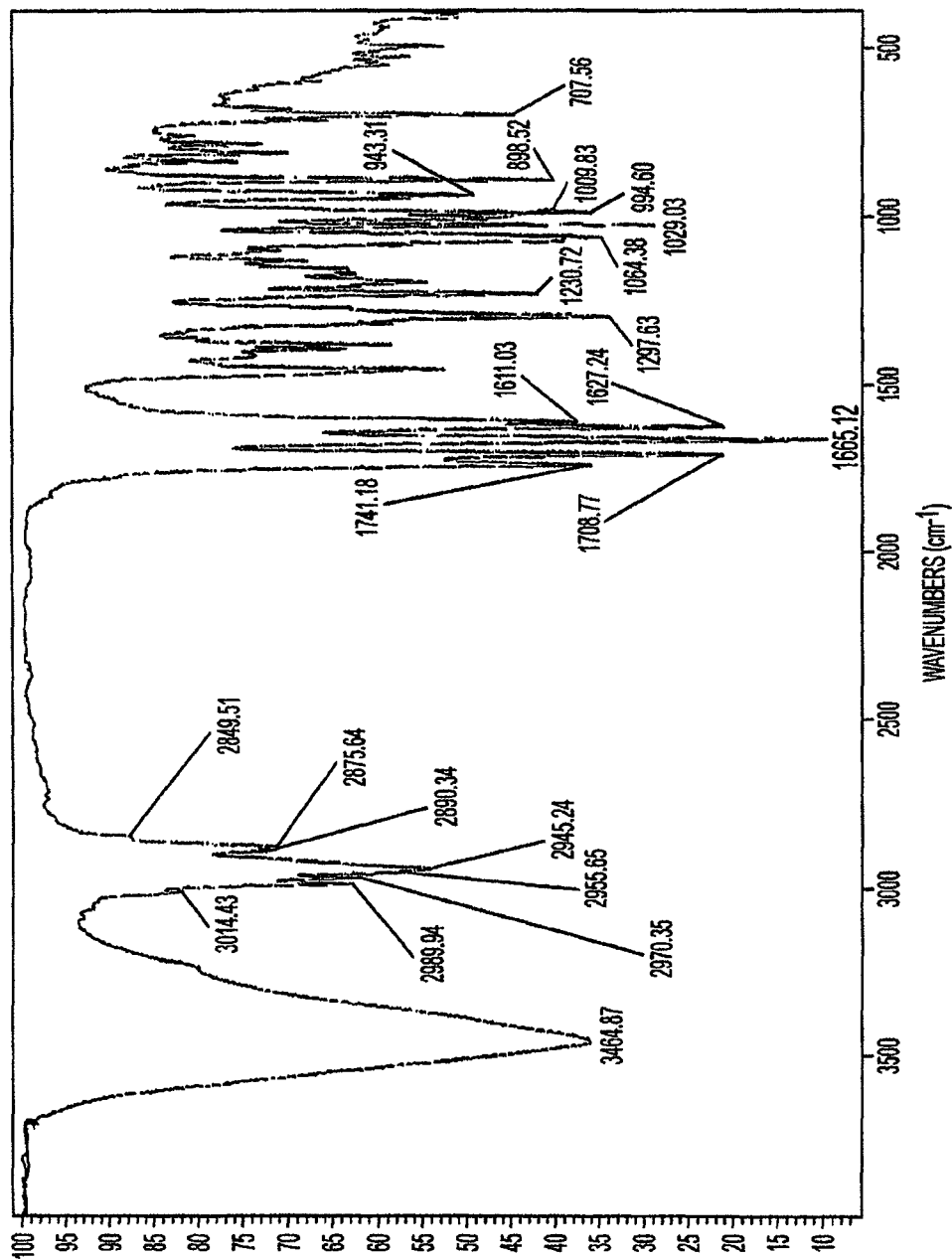
FIG. 3 depicts an infrared (IR) spectrum of the crystalline form of halobetasol propionate at laboratory scale, obtained after recrystallizing from absolute ethanol and drying in vacuum oven.

Recrystallization Using 100% Ethanol (Laboratory Scale) to Obtain Crystalline Form of Halobetasol Propionate Halobetasol propionate (1 gram) was added to absolute ethanol (5 mL; anhydrous alcohol). The resulting mixture was stirred and heated at about 80° C. until the halobetasol was dissolved. The solution was allowed to cool to room temperature and filtered. The resulting precipitate was filtered and washed twice with the absolute ethanol reaction liquid. The sample was dried in vacuum oven at 60° C. Characterization of the samples by IR absorption peaks showed peaks at 1741, 1709, 1665, 1627, and 1611±4 cm$^{-1}$. FIG. 3 shows the infrared spectroscopy of the obtained crystalline.

Figure 4:
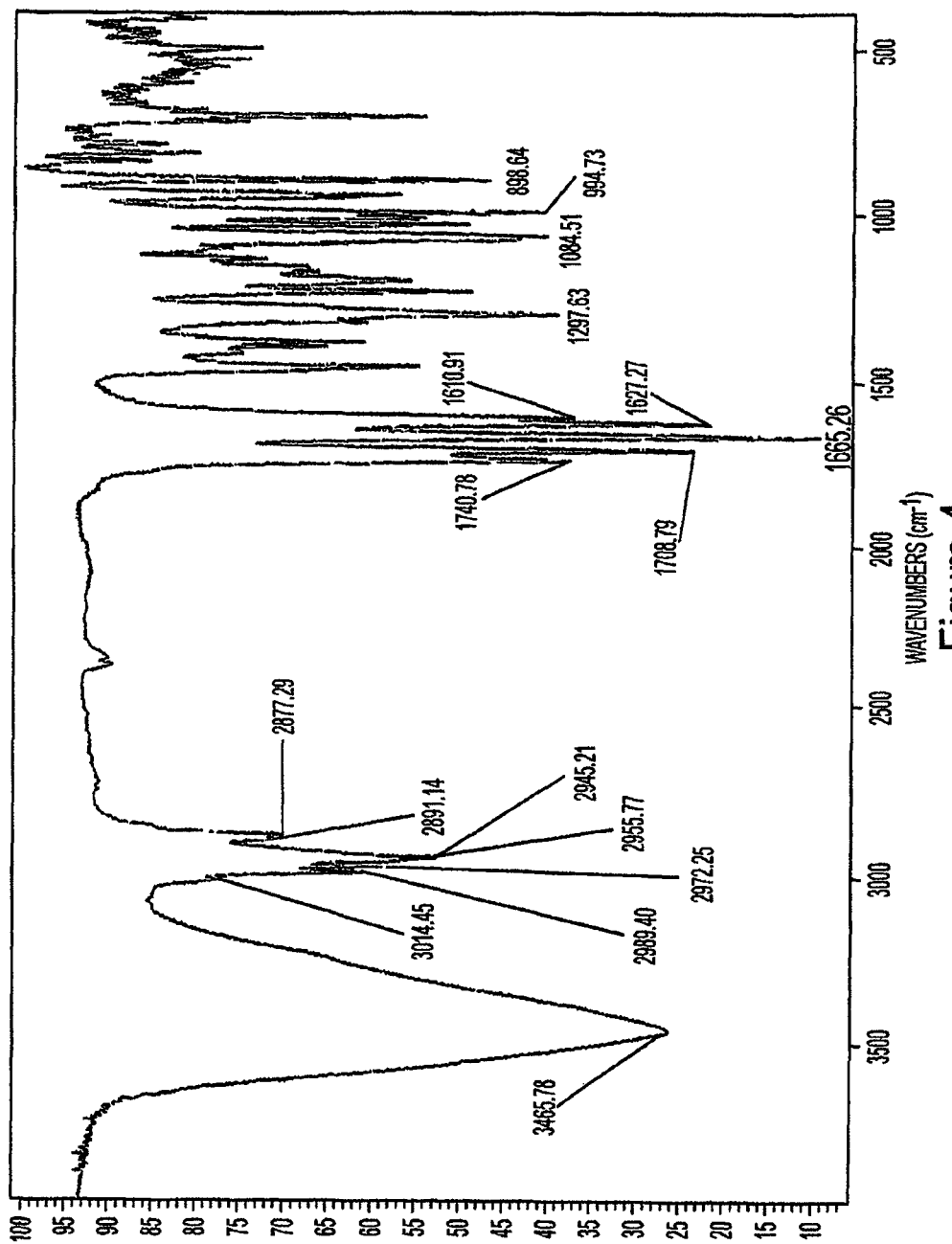
FIG. 4 depicts an infrared (IR) spectrum of the crystalline form of halobetasol propionate at laboratory scale, obtained after recrystallizing from absolute ethanol and drying overnight on open air for 24 hours.

In an analogous study, halobetasol propionate (1 gram) was recrystallized from absolute ethanol (5 mL) as described above in this Example. Instead of drying in vacuum over at 60° C., product was dried overnight on open air for 24 hours. FIG. 4 depicts the IR spectrum of the obtained sample under this drying condition. Comparison of IR spectrum between these two different drying conditions (i.e., vacuum oven at 60° C. vs. dried overnight on open air for 24 hours) reveals that the same crystalline form of halobestaol propionate was obtained after crystallization from absolute ethanol despite the difference in the drying conditions.

Example 6

Figure 5:
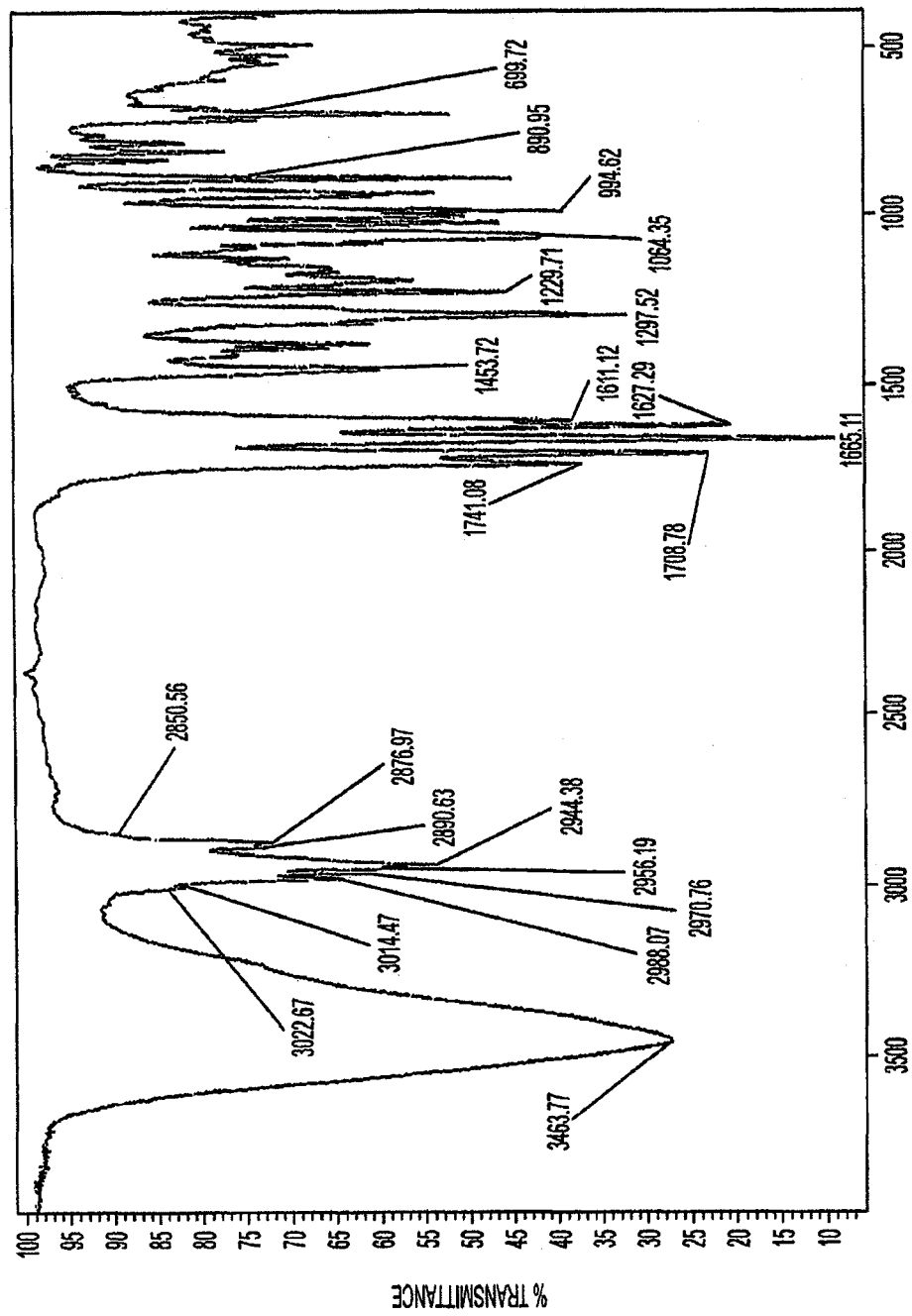
FIG. 5 depicts an infrared (IR) spectrum of the crystalline form of halobetasol propionate at laboratory scale, obtained after recrystallizing from a mixture of ethanol and water (v/v=95:5) and drying in vacuum oven.

Recrystallization Using 95% Ethanol (Laboratory Scale) to Obtain Crystalline Form of Halobetasol Propionate Halobetasol propionate (1 gram) was added to 95% ethanol (5 mL; a mixture of ethanol and water at v/v of 95:5). The resulting mixture was stirred and heated at about 80° C. until the halobetasol was dissolved. The solution was allowed to cool to room temperature and filtered. The resulting precipitate was filtered and washed twice with the 95% ethanol reaction liquid. The sample was dried in vacuum over at 60° C. Characterization of the samples by IR absorption peaks showed peaks at 1741, 1709, 1665, 1627, and 1611±4 cm$^{-1}$. FIG. 5 shows the infrared spectroscopy of the obtained crystalline. These studies show that the same crystalline form of halobetasol propionate (i.e., Form III) was obtained after crystallization using a mixture of ethanol and water either at a laboratory scale or a commercial scale.

In an analogous study, halobetasol propionate (1 gram) was recrystallized from 95% ethanol (5 mL) as described above in this Example. Instead of drying in vacuum over at 60° C., product was dried overnight on open air for 24 hours and 48 hours. Identical IR spectra were obtained (data not shown) under these drying conditions, indicating that the same crystalline form of halobestaol propionate was obtained after crystallization from 95% ethanol despite different drying conditions and duration.

Example 7

Figure 6:
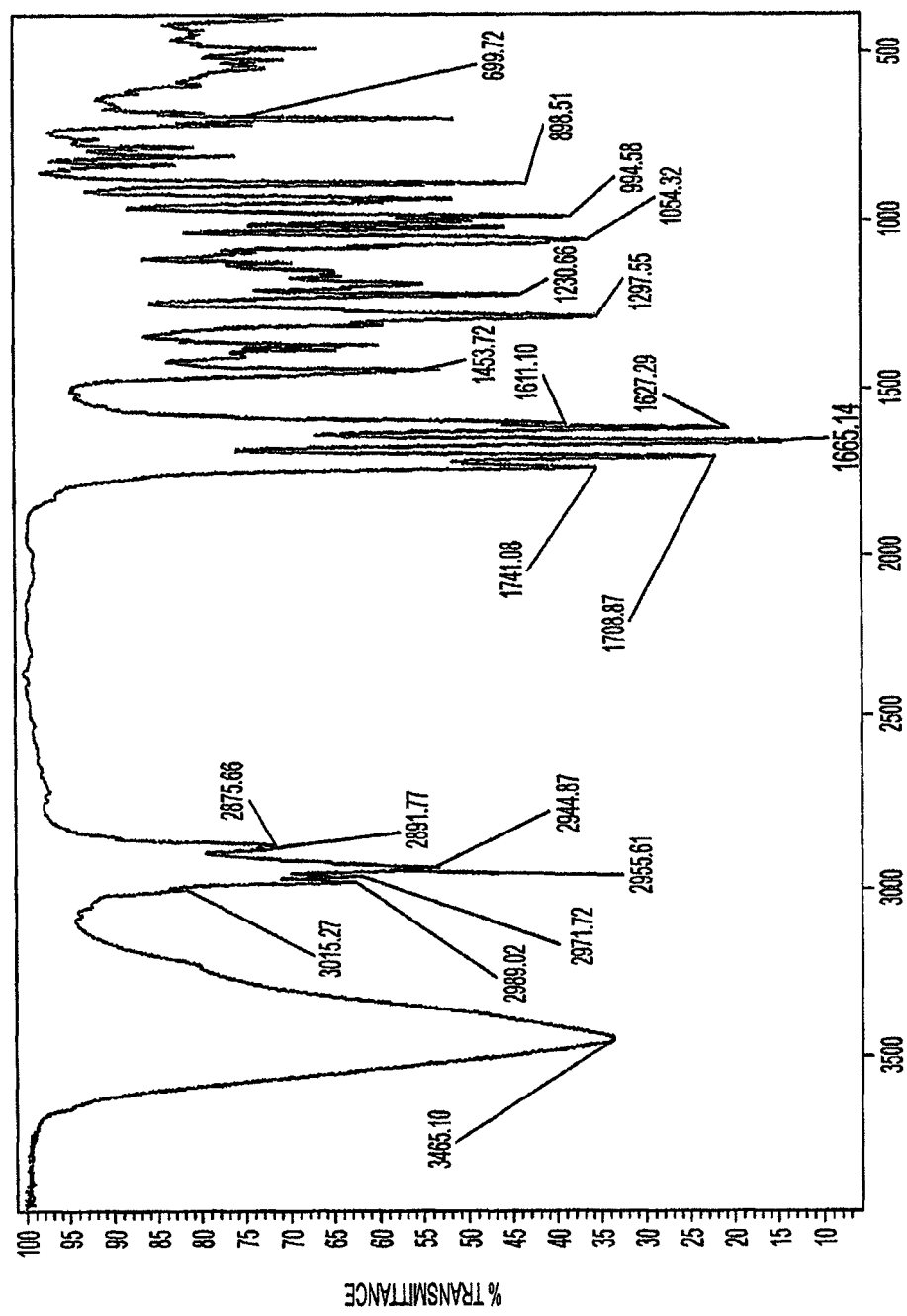
FIG. 6 depicts an infrared (IR) spectrum of the crystalline form of halobetasol propionate at laboratory scale, obtained after recrystallizing from a mixture of ethanol and water (v/v=80:20) and drying in vacuum oven.

Recrystallization Using 80% Ethanol (Laboratory Scale) to Obtain Crystalline Form of Halobetasol Propionate Halobetasol propionate (1 gram) was added to 80% ethanol (5 mL; a mixture of ethanol and water at v/v of 80:20). The resulting mixture was stirred and heated at about 80° C. until the halobetasol was dissolved. The solution was allowed to cool to room temperature and filtered. The resulting precipitate was filtered and washed twice with the 80% ethanol reaction liquid. The sample was dried in vacuum oven at 60° C. Characterization of the samples by IR absorption peaks showed peaks at 1741, 1709, 1665, 1627, and 1611±4 cm$^{-1}$. FIG. 6 shows the infrared spectroscopy of the obtained crystalline.

In an analogous study, halobetasol propionate (1 gram) was recrystallized from 80% ethanol (5 mL) as described above in this Example. Instead of drying in vacuum over at 60° C., product was dried overnight on open air for 24 hours and 48 hours. Identical IR spectra were obtained (data not shown) under these drying conditions, indicating that the same crystalline form of halobestaol propionate was obtained after crystallization from 80% ethanol despite different drying conditions and duration.

The citation and discussion of references in this specification is provided merely to clarify the description of the present invention and is not an admission that any such reference is "prior art" to the invention described herein. Each reference cited in this specification is incorporated herein by reference in its entirety.

What is claimed is:

1. A process for preparing a crystalline form of halobetasol propionate, comprising the step of crystallizing a single batch of at least about 100 grams of halobetasol propionate by
    (a) heating to a reflux temperature, halobetasol propionate in absolute ethanol or a mixture of between about 80:20 and about 100:0 ethanol:water;
    (b) cooling the solution to induce precipitation,
wherein the crystalline form of halobetasol propionate is characterized by an x-ray powder diffraction pattern having peaks at 10.0, 11.6, 12.9, 13.4, 14.5, 16.4, 17.6, and 23.5±0.2 degrees 2-theta.

2. The process of claim 1, wherein the crystalline form of halobetasol propionate is further characterized by an infrared spectrum having absorption peaks at 1741, 1709, 1665, 1627, and 1611±0.4 cm$^{-1}$.

3. The process of claim 1, wherein step (b) is performed by adding water to the prepared solution.

4. The process of claim 1, wherein step (b) is performed by adding water to the prepared solution over the course of about 30 minutes to about 90 minutes.

5. The process of claim 1, further comprising the step of isolating the crystallized halobetasol propionate after step (b).

6. The process of claim 1, wherein the crystallizing step is repeated at least once.

7. The process of claim 1, wherein the crystalline form of halobetasol propionate contains about 0.1% w/w or less of each individual impurity.

8. The process of claim 1, wherein the crystalline form of halobetasol propionate contains about 0.02% w/w or less of diflorasone.

9. The process of claim 1, wherein the crystalline form of halobetasol propionate contains about 0.02% w/w or less of halobetasol.

10. The process of claim 1, wherein the crystalline form of halobetasol propionate contains about 0.03% w/w or less of diflorasone 21-propionate.

11. The process of claim 1, wherein the crystalline form of halobetasol propionate contains about 0.03% w/w or less of diflorasone 17-propionate 21-mesylate.

12. The process of claim 1, wherein the crystalline form of halobetasol propionate contains about 0.05% w/w or less of 6-alpha,9-alpha-difluoro-10-hydroxy-16-beta-methyl-3-oxoandrosta-1,4-diene-17(R)-spiro-2'-[4'-chloro-5'-ethylfuran-3-(2'H)-one].

13. The process of claim 1, wherein the crystalline form of halobetasol propionate is prepared as a single batch of at least about 500 grams.

14. The process of claim 1, wherein the crystalline form of halobetasol propionate is prepared as a single batch of at least about one kilogram.

15. A process for preparing a crystalline form of halobetasol propionate, comprising the steps of: (a) crystallizing a single batch of at least about 100 grams of halobetasol propionate from a first ethanol solution by heating to a reflux temperature, halobetasol propionate in absolute ethanol or a mixture of between about 80:20 and about 100:0 ethanol:water; (b) cooling the solution to induce precipitation; (c) isolating the crystallized halobetasol propionate from the first ethanol solution; (d) crystallizing the isolated halobetasol propionate from a second ethanol solution by heating to a reflux temperature, halobetasol propionate in absolute ethanol or a mixture of between about 80:20 and about 100:0 ethanol:water; (e) cooling the solution to induce precipitation; (f) isolating the crystallized halobetasol propionate from the second ethanol solution, wherein the crystalline form of halobetasol propionate is characterized by an x-ray powder diffraction pattern having peaks at 10.0, 11.6, 12.9, 13.4, 14.5, 16.4, 17.6, and 23.5±0.2 degrees 2-theta.

16. The process of claim 15, wherein the first ethanol solution comprises water.

17. The process of claim 15, wherein the second ethanol solution comprises water.

18. The process of claim 15, wherein the crystalline form of halobetasol propionate is prepared as a single batch of at least about 500 grams.

19. The process of claim 15, wherein the crystalline form of halobetasol propionate is prepared as a single batch of at least about one kilogram.

* * * * *